United States Patent [19]

Verlier

[11] Patent Number: 4,915,692

[45] Date of Patent: Apr. 10, 1990

[54] NON-REUSABLE SYRINGE

[76] Inventor: Jacques Verlier, 16, rue Michel-Servet, 1206 Geneve, Switzerland

[21] Appl. No.: 291,572

[22] Filed: Dec. 29, 1988

[30] Foreign Application Priority Data

Dec. 30, 1987 [CH] Switzerland .......................... 5103/87
Dec. 12, 1988 [WO] PCT Int'l Appl. ... PCT/EP88/01141

[51] Int. Cl.⁴ .............................................. A61M 5/00
[52] U.S. Cl. .................................... 604/110; 604/218; 604/228
[58] Field of Search ................. 604/110, 218, 187, 228

[56] References Cited

U.S. PATENT DOCUMENTS 4,391,272 7/1983 Staempfli ........................... 604/110
4,781,684 11/1988 Trenner .............................. 604/110

FOREIGN PATENT DOCUMENTS 1791293 12/1975 Fed. Rep. of Germany .
2204429 5/1974 France .
2015883A 9/1979 United Kingdom .
2117249A 10/1983 United Kingdom .

Primary Examiner—John D. Yasko
Attorney, Agent, or Firm—Woodard, Emhardt, Naughton Moriarty & McNett

[57] ABSTRACT

A non-reusable syringe is disclosed having a syringe barrel and a plunger assembly reciprocable in the barrel. The plunger assembly comprises a plunger rod and a piston member, arranged so as to allow limited relative movement with respect to each other. The plunger rod has a resilient blocking member capable of becoming engaged with recesses in the inside wall of the syringe barrel. A safety member is removably arranged between the barrel and the plunger assembly to prevent blocking of the plunger rod before use of the syringe and define a precise dose of the liquid to be injected.

The present syringe offers practically absolute guarantee against re-use and allows better and quicker clearance of the air before the injection.

19 Claims, 3 Drawing Sheets

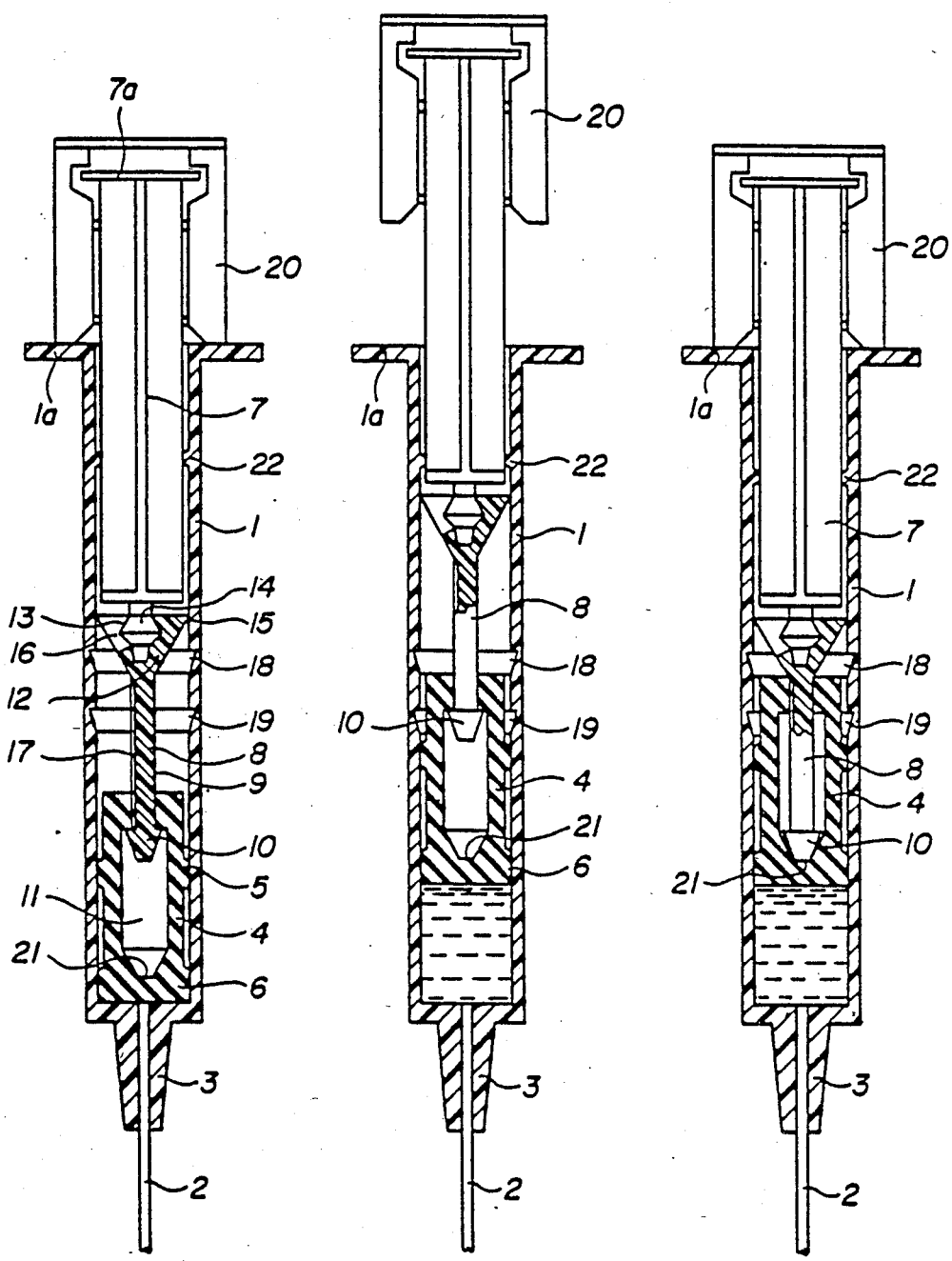

NON-REUSABLE SYRINGE

The present invention relates to a non-reusable syringe, i.e. a disposable syringe which can only be used once for making an injection.

The need for non-reusable syringes has become extremely urgent with a view to the increasing risk of propagating diseases which are transmissible by the human blood, such as viral hepatitis or AIDS, due to the re-use without sterilization or with insufficient sterilization of syringes which have already been used for an injection on somebody contaminated with the virus of such diseases. This is the more important as it is a current practice among drug addicts to re-use syringes already used by other persons without previous sterilization. The risk of contamination is also very high in the world's poorest countries due to the shortage of medical staff and the frequent lack of efficient sterilization means.

A number of non-reusable syringe structures have therefore been proposed for some time. However, the solutions of the prior art are not entirely satisfactory, either because of their too great complexity leading to an excessive cost price, or because of a lack of reliability, or because of other deficiencies, such as a difficult clearing of the air in the syringe before the injection, or an insufficient safety against all ways of re-using the syringe.

The main objects of the invention are to provide a relatively simple and economic syringe which offers a practically absolute guarantee of non-reusability and which allows to quickly and completely clear the air from the syringe before the injection. The invention has in particular for object to improve a disposable syringe as described in U.S. Pat. No. 4,391,272.

These and other objects and advantages of the invention will appear from the following description and claims.

The non-reusable syringe, according to the invention, has a hollow syringe barrel with a first open end adapted for receiving a hypodermic needle, and a second open end opposite said first end, a plunger assembly reciprocable in said syringe barrel, said assembly comprising a plunger rod and a piston member, said plunger rod comprising resilient blocking means having at least one peripheral portion tending to be applied to the inside wall of said syringe barrel, said inside wall having at least a first recess with a substantially sharp edge, said recess extending from said edge towards said first open end of the syringe barrel, said peripheral portion of said resilient means being arranged, so as to be capable of becoming engaged with said edge to prevent a retraction of the plunger rod in the direction of said second open end of the syringe barrel beyond a position in which said peripheral portion is engaged with said edge. According to the invention, said plunger assembly is arranged so as to allow a limited relative movement of the plunger rod with respect to the piston member.

In one embodiment of the invention, an end portion of the plunger rod is slidably connected with the piston member, so as to allow said limited relative movement. The plunger rod preferably comprises two separable parts, namely an actuating rod and a connection member, one end of the latter being releasibly connected with the actuating rod and the other end being slidably connected with the piston member. The piston member preferably contains an elongated cavity receiving an appendix of the plunger rod or of the connection member, said appendix being slidably arranged between a first position in which it is engaged with the piston member to allow retraction of the same in the direction of said second open end of the syringe barrel, and a second position in which it abuts against a bottom wall part of the piston member.

In a preferred embodiment, the inside wall of the syringe barrel has a second recess, the edge of which is arranged in the neighbourhood of said first recess between the latter and said second open end of the syringe barrel. A third recess can be provided with its edge arranged between the edge of said second recess and said second open end of the syringe barrel. The recesses can be annular grooves, or can be formed by a step-like increase of the diameter of the inside wall of the syringe barrel, the edges of the recesses being circular and said resilient blocking means having at least one peripheral rim portion capable of becoming engaged with said circular edges.

The syringe according to the invention further preferably comprises at least one removable safety member, arranged so as to prevent the plunger assembly from being forced, prior to use, in a position in which the resilient blocking means of the plunger rod becomes engaged with the first or second recesses in the inside wall of the syringe barrel.

The invention will be better understood by reference to the description which is to follow, and by reference to the accompanying drawings in which are illustrated, diagrammatically and by way of example, two constructional forms of the syringe according to the invention.

FIG. 1 is a view, in longitudinal axial section, of a first embodiment of he syringe according to the invention in its original state, before it is used, i.e. the state in which it is stored and shipped;

FIG. 2 is a view similar to FIG. 1, showing a state in which the syringe of FIG. 1 is being filled with the liquid to be injected;

FIG. 3 is a view similar to that of FIG. 1, showing the state of the syringe of FIG. 1 in which the same is prepared for an injection;

Figure 4:
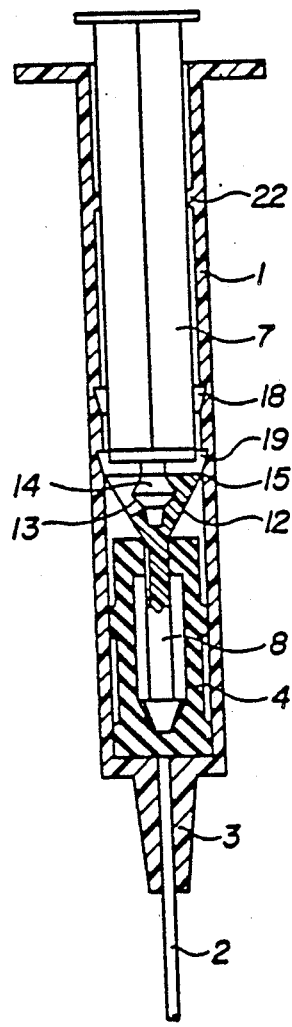
FIG. 4 is a view similar to that of FIG. 1, showing the state of the syringe of FIG. 1 after a complete injection has been carried out.

The syringe shown in FIGS. 1 to 6 comprises a barrel 1, essentially in the form of a hollow cylinder having a first open end 3 adapted to receive a hypodermic needle 2. A second open end of the barrel 1 is provided with a flat gripping member 1a and has an upper portion of an actuating rod 7 with a disk-shaped gripping and actuating member 7a extending through it. The actuating rod 7 is part of a plunger assembly which is reciprocable in the syringe barrel 1 and further comprises, in the present example, a connecting member 8 and a piston member 4. The piston member 4 is provided with two protruding annular portions 5 and 6, the latter forming the lower end portion of the piston member, allowing sliding of the piston member along the lower part of the cylindrical inside wall of barrel 1, while providing a tight partition between the lower end portion of piston member 4 and the syringe barrel.

Piston member 4 has a substantially cylindrical cavity 11 extending longitudinally between a bottom wall portion of the piston member forming a seat 21, and an opening in the upper end portion of the piston member. Connection member 8 has a substantially cylindrical body part 9 and a substantially frustroconical appendix 10 inserted through the opening of the piston member to be slidable inside the cavity 11. A longitudinal groove 17 is provided on the body part 9 to allow the passage of air between the cavity 11 and the syringe barrel while the body part 9 is narrowly guided in the opening of piston member 4 during its sliding movement.

The upper part of connection member 8 is formed by a generally frustroconical blocking member 12 which is divided into a number of sections, for example three separated by radially extending slots 16. Each section has a rim portion 15, as shown in FIG. 1, which is resiliently applied against the inside wall of barrel 1. The barrel 1 and the parts of the plunger rod are preferably made of synthetic resins, having adequate rigidity as required by their function. The piston member is here preferably made of rubber or a similar resilient material. Portion 12 of the connection member 8 has such a shape that the diameter of the rim 15 in its free state, before it is mounted inside the barrel 1, is slightly larger than the greatest diameter of the inside wall of barrel 1. This means that, in the position shown in FIG. 1, the said sections of member 12 are slightly radially compressed, the rim portions 15 being resiliently applied against the inside wall of barrel 1. Member 12 further has a flared axial cavity 13 with an inside latching edge, the shape of which corresponds, in the state represented in FIG. 1, to the shape of a fixing neck portion 14 formed at the lower end of the actuating rod 7. The fixing neck 14 is thus retained in the cavity 13 in the position shown in FIG. 1 and allows, in particular, retraction of the whole plunger assembly from that position in which, as shown in FIG. 1, the appendix 10 of the connection member 8 is engaged with the piston member 4, a shoulder of appendix 10 bearing against a corresponding wall portion surrounding the opening of cavity 11.

Annular recesses 18 and 19 are shown as frustroconical grooves in the inside wall of barrel 1, each groove having a relatively sharp, circular upper edge. A third recess is formed in the inside wall of barrel 1 by a step-like increase of the inner diameter thereof, between an annular guiding portion 22 in the upper part of the barrel, and the lower portion of the barrel containing the piston member.

The present syringe is further provided with a removable safety member 20 which is formed, for example, integral with the actuating rod 7 around the upper end portion thereof, so as to define a precise position of maximum penetration of the actuating rod into the barrel 1. This maximum penetration before the actual injection defines the precise dose of the liquid to be injected, as will be seen from the further description hereafter. Member 20 can comprise a number of radially arranged blades or wings having an integral top portion and being detachably connected with the actuating rod 7, the lower end portion of said blades abutting against the gripping member 1a of the barrel. Breaking off the lateral connections of the blades with the actuating rod allows to remove the whole safety device 20. Other forms of removable members originally either integral with the barrel 1 or with the actuating rod 7 can be arranged to fulfill the same purpose.

The operation of the present syringe and the function of the various parts mentioned above, will become apparent from the description of the various states of the syringe according to FIGS. 2 to 6.

The present syringe is delivered and stored, prior to being used, in the state shown in FIG. 1.

When the syringe is to be used for an injection, it is first filled in the usual manner by drawing in the liquid to be injected by pulling the actuating rod 7 rearwardly, as illustrated by FIG. 2.

The syringe will generally be filled up to a position of the plunger rod in which the rim 15 of member 12 abuts against the edge of the annular member 22, or slightly below. The respective lengths of the various parts of the syringe are so chosen that the maximum filling volume corresponding to the maximum retraction of the actuating rod is slightly greater than the actual dose to be injected. In that case, the air remaining with the liquid can be cleared by pushing the actuating rod down to a position in which the safety member 20 abuts against the gripping member 1a as shown in FIG. 3. When comparing this state of the syringe with that of FIG. 1, it will be seen that the plunger rod formed by the actuating rod 7 and the connection member 8 is in the same position, but that the piston member 4 is shifted to a position in which the seat 21 abuts against the appendix 10 of the connection member. It is to be noted that this shifting, as provided by the present arrangement, allows, in the original state of the syringe, the piston member 4 to be placed in its lowest position as shown in FIG. 1, thus reducing the air to be cleared from the syringe after filling practically to the volume of the needle channel. Clearing of the air will therefore be much quicker and easier as compared with the clearing of the prior art syringes, in which a certain volume of air was necessarily present in the original state of the syringe, since the piston member could not be placed against the bottom of the barrel prior to filling.

When making the injection, the so-called "vein test" may first be carried out to determine the presence or absence of blood in the needle, and thus a proper location of the needle in the patient. For this "vein test", the actuating rod is again rectracted slightly beyond the position shown in FIG. 2, thus drawing a small quantity of fluid from the patient while the needle is inserted. For subsequently injecting the whole quantity of liquid contained in the syringe, the safety member 20 is removed from the actuating rod and the same is pushed down until the final position shown in FIG. 4 is reached. After completion of the injection, the syringe is withdrawn and disposed of.

Figure 5:
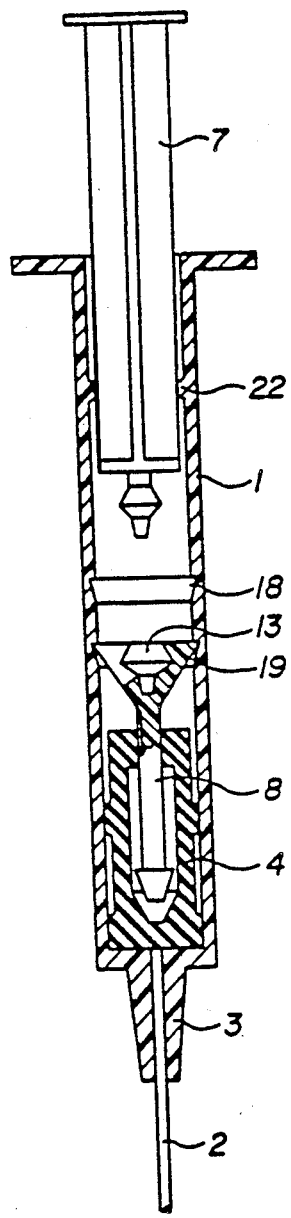
FIG. 5 is a view similar to that of FIG. 1, showing the state of the syringe of FIG. 1 after an attempt to retract the piston member from its end position in the barrel after an injection.

FIG. 5 shows what happens when, after a first injection, one tries to fill the syringe again by retracting the actuating rod 7. The connection member 8 will first follow the actuating rod 7 up to a position in which the rim portion of member 12 becomes engaged with the edge of recess 19, thereby blocking a further upward movement of the connection member. An additional safety measure is provided in the present embodiment by the fact that the cavity 13 of the resilient member 12 expands radially when in the position shown in FIG. 5, the resilient rim portions enter the recess 19, and the conical neck member of the actuating rod 7 thus becomes detached from the connection member 8 when further retraction is attempted. The position of the edge of the recess 19 is preferably chosen close to the actual end position of the piston member 4, so that the piston member can only effect a very small upward movement from the position of FIG. 5, i.e. until the bottom wall of the piston member 4 abuts against the appendix of the connection member 8. This means that a new filling of the syringe is not only impossible by retracting the actuating rod, but also any attempt to act on the piston member through the opening of the barrel on the needle-side end thereof will be unsuccessful.

Figure 6:
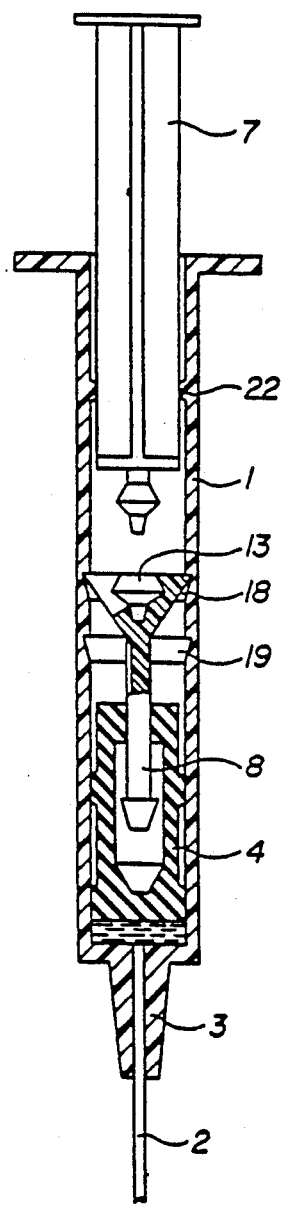
FIG. 6 is a view similar to that of FIG. 1, showing the state of the syringe of FIG. 1 after an attempt to retract the piston member from a position reached by an incomplete injection, i.e. a position preceding the end position of the piston member.

FIG. 6 shows the state of the syringe after another kind of attempt was made to re-use the same, namely by not injecting the whole quantity of liquid and thus not reaching the final position of the piston member in which the same becomes blocked. However, upon retraction of the actuating rod 7 from a position in which the connecting member 8 was not yet engaged with recess 19, the resilient blocking member 12 will become engaged with the edge of the second recess 18 placed slightly above that of recess 19. In that position, when a retracting force is applied to actuating rod 7, the same will again become disconnected from the connection member 8 in the same way as in the case of FIG. 5. It is, accordingly, not possible to move the piston member 4 upwards by means of the actuating rod 7 and, accordingly no additional liquid can be filled into the syringe by aspiration. The present syringe is thus completely un-reusable.

Figure 7:
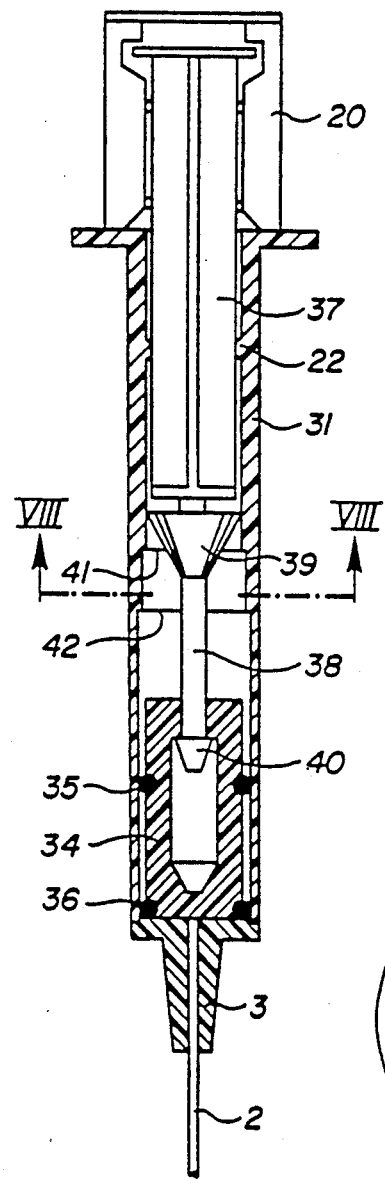
FIG. 7 is a view similar to that of FIG. 1, of a second embodiment of the syringe according to the invention, in its original state.
Figure 8:
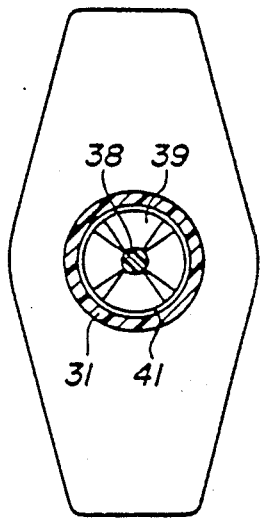
FIG. 8 is a cross-sectional view of the syringe of FIG. 7 along the line VIII—VIII of FIG. 7.

Another, but similar embodiment of the syringe of the invention is shown in FIG. 7 which corresponds to FIG. 1 and illustrates the original state of the syringe according to this other embodiment. In this case, the actuating part and the connection part of the plunger rod are made integral with each other and not separable. The plunger rod has an upper actuating portion 37, a blocking portion 39, a rod-shaped portion 38 and an appendix 40. The cross-sectional view of FIG. 8 shows, in particular, the blocking portion 39, comprising for example four segments separated by small radial slots to form a resilient blocking portion cooperating with recesses in the inside wall of the barrel 31 of this embodiment. The inside wall of barrel 31 comprises, in particular, recesses 41 and 42, formed as step-like increases of the inner diameter of the barrel towards the bottom of the barrel containing the piston member 34. The resilient blocking portion 39 cooperates with the edges of recesses 41 and 42, in a similar manner as in the previous embodiment of FIG. 1, and the operation of this syringe is thus substantially the same. The main difference results from the mentioned fact that the actuating portion 37, and the connection portion 38, are not separable and, therefore, the additional safety as mentioned in connection with FIGS. 5 and 6 is not present in this embodiment. It is to be noted that the step-like configuration of recesses 41 and 42 facilitates the manufacture of the syringe barrel by moulding and reduces the cost price thereof. Another structural difference which is capable of allowing a reduction of the cost price, consists in making a body part of the piston member from a plastic material, rather than of rubber or similar, and to mount two 0-rings 35 and 36 or similar sealing means on that piston member body for providing the necessary tightness.

The various structural features mentioned in connection with the embodiment of FIG. 7 can of course also be applied separately or in combination in the embodiment according to FIG. 1. The basic functional advantages of the invention, namely the practically complete safety against re-use and the high reliability of operation remain present in any such combination or in any similar embodiment falling within the scope of the following claims.

I claim:

1. A non-reusable syringe having a hollow syringe barrel with a first open end adapted for receiving a hypodermic needle and a second open end opposite said first end, a plunger assembly reciprocal in said syringe barrel, said assembly comprising a plunger rod and a piston member, said plunger rod comprising resilient blocking means having at least one peripheral portion tending to be applied to the inside wall of said syringe barrel, said inside wall having at least a first recess with a substantially sharp edge, said recess extending from said edge towards said first open end of the syringe barrel, said peripheral portion of said resilient means being arranged so as to be capable of becoming engaged with said edge to prevent a retraction of the plunger rod in the direction of said second open end of the syringe barrel beyond a position in which said peripheral portion is engaged with said edge, said side plunger rod having a first end portion extending through said second open end of the syringe barrel, and a second end portion which is slidably connected with said piston member so as to allow a limited relative movement of said second end portion of said plunger rod with respect to said piston member.

2. A syringe according to claim 1, wherein the plunger rod comprises two separable parts, namely an actuating rod and a connection member having each first and second end portions, said first end portion of the actuating rod extending through said second open end of the syringe barrel and said second end portion of the actuating rod comprising means for releasably fixing said second end portion of the actuating rod to said first end portion of the connection member, said first end portion of the connection member comprising said resilient blocking means, and said second end portion of the connection member being slidably connected with said piston member, so as to allow said limited relative movement of said plunger rod with respect to said piston member.

3. A syringe according to claim 1, wherein said piston member has an elongated cavity arranged between an opening in the piston member through which extends said second end portion of the plunger rod and a bottom wall part of said piston member which is facing said first open end of the syringe barrel, said second end portion of the plunger rod comprising an appendix slidably arranged in said elongated cavity between a first position in which it is engaged with the piston member to allow retraction of the same in the direction of said second open end of the syringe barrel and a second position in which it abuts against said bottom wall part of the piston member.

4. A syringe according to claim 2, wherein said piston member has an elongated cavity arranged between an opening in the piston member through which extends said second end portion of the connection member and a bottom wall part of said piston member which is facing said first open end of the syringe barrel, said second end portion of the connection member comprising an appendix slidably arranged in said elongated cavity between a first position in which it is engaged with the piston member to allow retraction of the same in the direction of said second open end of the syringe barrel and a second position in which it abuts against said bottom wall part of the piston member.

5. A syringe according to claim 1, wherein said inside wall of the syringe barrel has a second recess with a substantially sharp edge arranged in the neighbourhood of said first recess between the latter and said second open end of the syringe barrel.

6. A syringe according to claim 5, wherein said inside wall of the syringe barrel has a third recess with a substantially sharp edge arranged between said edge of said second recess and said second open end of the syringe barrel.

7. A syringe according to claim 1, wherein said first recess is an annular groove in said inside wall of the syringe barrel and said edge thereof is circular, said resilient blocking means having at least one peripheral rim portion capable of becoming engaged with said circular edge.

8. A syringe according to claim 5, wherein said first and second recesses are annular grooves in said inside wall of the syringe barrel and said edges thereof are circular, said resilient blocking means having at least one peripheral rim portion capable of becoming engaged with said circular edges.

9. A syringe according to claim 6, wherein at least two of said first, second and third recesses are annular grooves in said inside wall of the syringe barrel and said edges of said at least two recesses are circular, said resilient blocking means having at least one peripheral rim portion capable of becoming engaged with said circular edges.

10. A syringe according to claim 1, wherein said first recess is formed by a step-like increase of the diameter of said inside wall of the syringe barrel, said edge of said first recess being circular and said resilient blocking means having at least one peripheral rim portion capable of becoming engaged with said circular edge.

11. A syringe according to claim 5, wherein said first and second recesses are each formed by a corresponding step-like increase of the diameter of said inside wall of the syringe barrel and said edges of said first and second recesses are circular, said resilient blocking means having at least one peripheral rim portion capable of becoming engaged with said circular edges.

12. A syringe according to claim 6, wherein at least two of said first, second and third recesses are formed by a corresponding step-like increase of the diameter of said inside wall of the syringe barrel and said edges of said at least two recesses are circular, said resilient blocking means having at least one peripheral rim portion capable of becoming engaged with said circular edges.

13. A syringe according to claim 1, comprising at least one removable safety member arranged so as to prevent the plunger assembly from being forced, prior to use, in a position in which said resilient blocking means of the plunger rod becomes engaged with said edge of said first recess in the inside wall of the syringe barrel.

14. A syringe according to claim 5, comprising at least one removable safety member arranged so as to prevent the plunger assembly from being forced, prior to use, in a position in which said resilient blocking means of the plunger rod becomes engaged with said edge of said second recess in the inside wall of the syringe barrel.

15. A syringe according to claim 6, comprising at least one removable safety member arranged so as to prevent the plunger assembly from being forced, prior to use, in a position in which said resilient blocking means of the plunger rod becomes engaged with said edge of said second recess in the inside wall of the syringe barrel.

16. A syringe according to claim 8, comprising at least one removable safety member arranged so as to prevent the plunger assembly from being forced, prior to use, in a position in which said resilient blocking means of the plunger rod becomes engaged with said edge of said second recess in the inside wall of the syringe barrel.

17. A syringe according to claim 9, comprising at least one removable safety member arranged so as to prevent the plunger assembly from being forced, prior to use, in a position in which said resilient blocking means of the plunger rod becomes engaged with said edge of said second recess in the inside wall of the syringe barrel.

18. A syringe according to claim 11, comprising at least one removable safety member arranged so as to prevent the plunger assembly from being forced, prior to use, in a position in which said resilient blocking means of the plunger rod becomes engaged with said edge of said second recess in the inside wall of the syringe barrel.

19. A syringe according to claim 12, comprising at least one removable safety member arranged so as to prevent the plunger assembly from being forced, prior to use, in a position in which said resilient blocking means of the plunger rod becomes engaged with said edge of said second recess in the inside wall of the syringe barrel.

* * * * *